(12) United States Patent
Bakharev et al.

(10) Patent No.: US 10,041,863 B2
(45) Date of Patent: Aug. 7, 2018

(54) METHOD OF MEASURING CARBONATION LEVELS IN OPEN-CONTAINER BEVERAGES

(71) Applicant: PepsiCo, Inc., Purchase, NY (US)

(72) Inventors: Aleksey Bakharev, Niskayuna, NY (US); Herriot Moise, Putnam Valley, NY (US); Min Feng Zheng, Flushing, NY (US)

(73) Assignee: PepsiCo, Inc., Purchase, NY (US)

( * ) Notice: Subject to any disclaimer, the term of this patent is extended or adjusted under 35 U.S.C. 154(b) by 226 days.

(21) Appl. No.: 14/678,258

(22) Filed: Apr. 3, 2015

(65) Prior Publication Data

US 2016/0290897 A1    Oct. 6, 2016

(51) Int. Cl.
| | | |
|---|---|---|
| G01N 1/22 | (2006.01) | |
| G01N 21/43 | (2006.01) | |
| G01N 33/00 | (2006.01) | |
| G01N 7/00 | (2006.01) | |
| G01N 33/14 | (2006.01) | |
| G01N 21/41 | (2006.01) | |

(52) U.S. Cl.
CPC ............ G01N 1/2226 (2013.01); G01N 7/00 (2013.01); G01N 21/43 (2013.01); G01N 33/004 (2013.01); G01N 33/14 (2013.01); G01N 21/4133 (2013.01); G01N 2001/2232 (2013.01); G01N 2001/2282 (2013.01); G01N 2001/2285 (2013.01)

(58) Field of Classification Search
CPC .... G01N 1/2226; G01N 21/43; G01N 33/004; G01N 2001/2232; G01N 2001/2285; G01N 2001/2282

USPC ..... 250/338.5, 343; 426/231–232, 590, 477; 73/19.01, 19.06

See application file for complete search history.

(56) References Cited

U.S. PATENT DOCUMENTS

| | | | |
|---|---|---|---|
| 3,849,070 A | * | 11/1974 | Garza ................. G01N 1/2226 422/68.1 |
| 4,208,903 A | | 6/1980 | Hopper et al. |
| 4,276,769 A | | 7/1981 | Wieland et al. |
| 4,302,314 A | * | 11/1981 | Golimowski ........ G01N 27/403 204/434 |
| 4,563,892 A | | 1/1986 | D'Aoust |
| 4,745,794 A | | 5/1988 | Steichen et al. |

(Continued)

OTHER PUBLICATIONS

Psychobat's variety channel, 16 Year Old Coke Taste Test, Sep. 27, 2014, YouTube.com, https://youtu.be/7oKQ31Wopok, Date accessed Nov. 2, 2016.*

(Continued)

*Primary Examiner* — David Porta
*Assistant Examiner* — Gisselle Gutierrez
(74) *Attorney, Agent, or Firm* — Sterne, Kessler, Goldstein & Fox P.L.L.C.

(57) ABSTRACT

Carbon dioxide levels in an open-container beverage are measured by transferring a quantity of the beverage to a vessel. A closure is secured onto the vessel to form an enclosed volume containing the beverage. A probe is inserted through the closure to contact the beverage, and a sample is transferred from the vessel to a measurement instrument to determine the carbon dioxide level. The methods allow for significantly greater precision and reliability in measuring carbonation levels of open-container beverages relative to currently available techniques.

18 Claims, 6 Drawing Sheets

(56) References Cited

U.S. PATENT DOCUMENTS

| | | | |
|---|---|---|---|
| 5,029,733 A * | 7/1991 | Hedderick | B67D 1/0004 |
| | | | 137/170.1 |
| 6,277,329 B1 | 8/2001 | Evans | |
| 6,874,351 B2 | 4/2005 | Bloder et al. | |
| 6,969,857 B2 | 11/2005 | Owen | |
| 2003/0029228 A1* | 2/2003 | Bloder | G01N 7/14 |
| | | | 73/53.01 |
| 2014/0065266 A1* | 3/2014 | Shalev | A47J 31/407 |
| | | | 426/89 |
| 2014/0147558 A1* | 5/2014 | Rasmussen | B65D 81/2053 |
| | | | 426/106 |

OTHER PUBLICATIONS

International Search Report and Written Opinion of the International Searching Authority for International Application No. PCT/US16/25229, dated May 27, 2016 (10 pages).

\* cited by examiner

METHOD OF MEASURING CARBONATION LEVELS IN OPEN-CONTAINER BEVERAGES

BACKGROUND

Carbon dioxide levels in beverages can significantly influence taste and other properties, such as mouthfeel. For this reason carbonation levels usually are carefully monitored during bottling operations. A number of instruments for determining the quantity of carbon dioxide in bottled beverages are commercially available. One common technique involves inserting a probe through the closure of a sealed container (e.g., beverage-filled can or bottle) and transferring a sample of the liquid to a measuring chamber. After the measuring chamber is closed, its volume is expanded via a flexible membrane or a piston-type injector fitted fluid-tight to the chamber. The equilibrium pressure established after the expansion and the sample temperature are then measured. Carbon dioxide content may then be calculated based on Henry's law. Bloder et al. U.S. Pat. No. 6,874,351 describes an instrument adapted to account for dissolved quantities of oxygen and nitrogen so that carbon dioxide levels may be measured more accurately.

Whereas such relatively precise measurement techniques are available for measuring carbonation levels in bottled beverages, these techniques are unsuitable for measuring carbonation levels in beverages in open-atmosphere conditions, such as beverages present in an opened container or which are dispensed from fountain equipment, for example. Techniques for measuring carbonation levels in open-container beverages generally employ a so-called "handshake" method, which involves placing a liquid sample into a measurement vessel and then shaking to achieve equilibrium pressure. The vessel often is equipped with a pressure gauge and thermometer, the readings from which can be used to calculate carbonation levels. Such techniques generally are less precise and less reliable than the aforementioned techniques used in connection with bottled beverages. Errors in measurement may be introduced not only from the equipment used, but also by the individuals making the measurements, including variations in techniques from one operator to the next. It would be desirable to develop a method for more precisely and more reliably measuring carbonation levels in open-container beverages.

SUMMARY

In one aspect, a method is provided for measuring carbon dioxide levels in an open-container beverage. A quantity of the beverage is transferred to a vessel to at least partially fill the vessel. A closure is then secured onto the vessel to form an enclosed volume containing the beverage. A probe is inserted through the closure to contact the beverage, and a sample is transferred from the vessel to a measurement instrument which is used to determine the carbon dioxide level.

The measurement instrument may employ a number of different principles for measuring carbon dioxide levels. In one technique, the volume of a measurement chamber is expanded and the equilibrium pressure of the expanded volume is measured. Based on the measured equilibrium pressure and temperature, the carbon dioxide level of the sample may be ascertained.

In another technique, a measuring instrument may use a selective membrane to determine carbon dioxide levels. The membrane is permeable to carbon dioxide but impermeable to other gases (nitrogen, oxygen, etc.). The amount of carbon dioxide passing through the selective membrane is measured, whereupon the amount of carbon dioxide present in the sample can be determined.

Yet another technique for measuring carbon dioxide levels utilizes infrared (IR) light. In this technique, a beam of IR light is passed through a liquid sample. The angle of refraction is measured and, based on the measured angle of refraction, the carbonation level of the sample can be determined.

The methods described herein allow for significantly greater precision and reliability in measuring carbonation levels of open-container beverages relative to currently available handshake techniques. The methods as described herein permit the use of more precise measuring instruments heretofore useful only with bottled beverages. Further, by avoiding the need for manually agitating (shaking) the beverage sample to achieve equilibrium pressure, measurements are more reliable and less prone to human error.

BRIEF DESCRIPTION OF THE DRAWINGS

A more complete understanding of the present invention and certain advantages thereof may be acquired by referring to the following detailed description in consideration with the accompanying drawings, in which.

DETAILED DESCRIPTION

Figure 1:
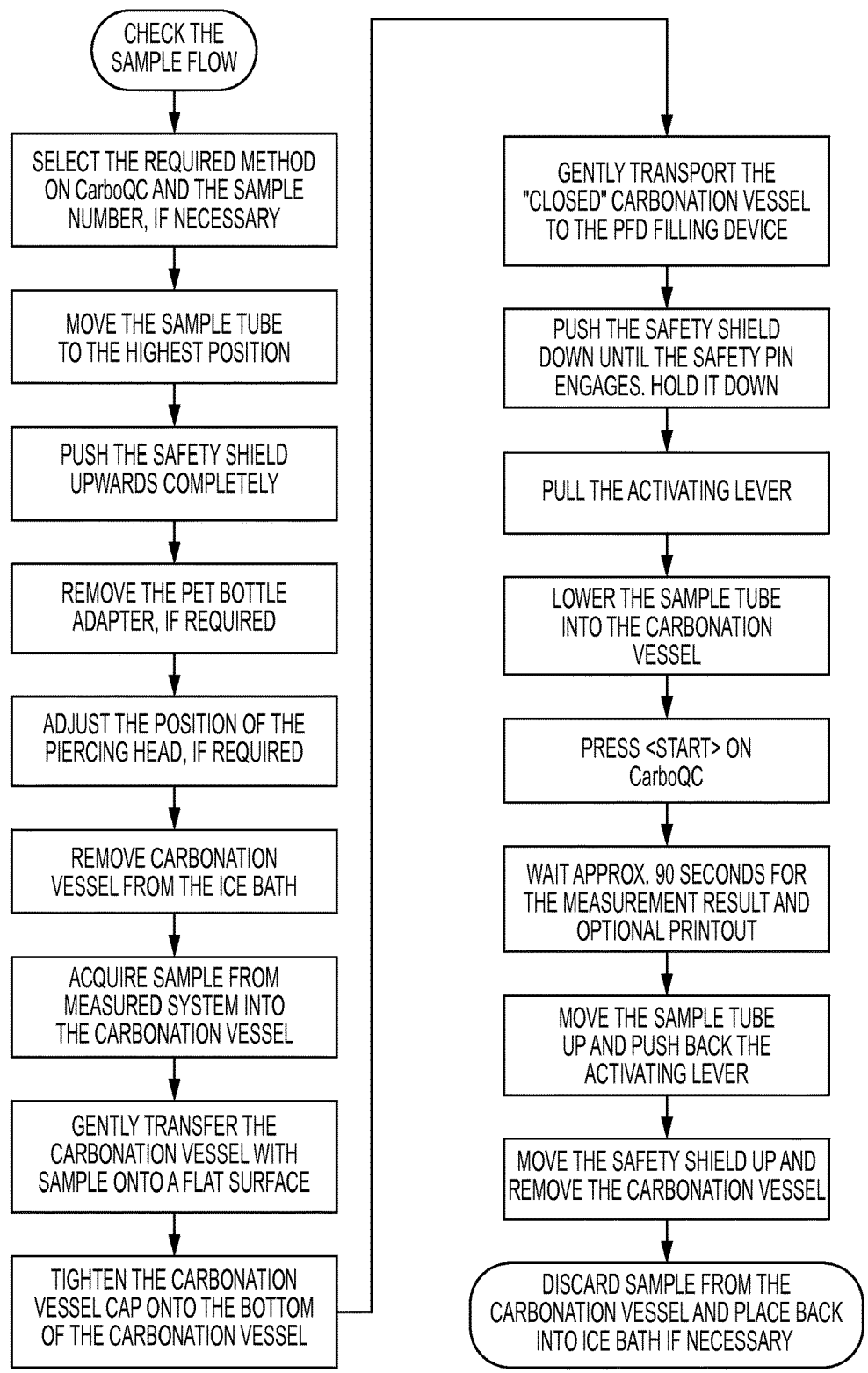
FIG. 1 is a flow diagram illustrating a method of measuring carbon dioxide levels in a beverage in accordance with one embodiment of the invention.

In general, the methods described herein are specifically adapted for measuring carbonation (carbon dioxide) levels in open-container beverages. As used herein, "open-container" refers to a beverage that has been opened after bottling operations, such as an opened can, or an opened plastic or glass bottle which may have been reclosed with a resealable (e.g., twist-top) closure. In some cases it may be useful to measure carbonation levels in an opened can to ascertain loss of carbonation after prescribed time interval(s). It also may be useful to measure carbonation levels in an opened-then-resealed carbonated soft drink (CSD) or carbonated water bottle after prescribed time interval(s) to measure any loss of carbonation. The term "open-container" and similar expressions also refer to uncontained beverages such as those dispensed from fountain equipment or the like. The methods described herein may be used for measuring carbonation levels of any type of carbonated beverages, including alcoholic and non-alcoholic beverages, e.g., soft drinks, fruit drinks, carbonated water, and the like.

The methods described herein may employ commercially available carbonation measuring instruments and a suitable carbonation vessel which may be adapted for use together with the particular instrument used. The details of suitable carbonation measuring instruments and carbonation vessels that may be used are discussed hereinbelow, although it should be emphasized that the invention is not limited to the details of the particular equipment illustrated herein. Rather, the principles set forth herein may be applied to various other types of measuring instruments and carbonation vessels, with suitable adaptions made, as may be necessary, that will be apparent to persons skilled in the art upon reading the present disclosure.

Carbonation Measuring Instrument

A variety of carbonation measuring instruments (sometimes referred to herein as "measuring instrument" or "instrument") may be used in connection with the methods described herein. Three general categories of instruments will be discussed hereinafter, although it should be recognized that the invention is not limited to these particular types of instruments. A first type of measuring instrument involves determining carbon dioxide levels based on Henry's law, in which the volume of a measurement chamber is expanded and the equilibrium pressure and equilibrium temperature of the expanded volume is measured. Based on the measured equilibrium pressure, equilibrium temperature, and the known volume, the carbon dioxide level of the sample may be ascertained.

In this particular type of instrument, the measuring chamber is expandable to allow for equilibrium pressure of a sample to be measured at one or more expanded volumes. One example of such an instrument is described in Bloder et al. U.S. Pat. No. 6,874,351, the disclosure of which is hereby incorporated by reference in its entirety. Such an instrument is commercially available from Anton Paar under the trade name CarboQC®. The instrument enables the effect that other dissolved gases in a sample liquid (especially nitrogen and oxygen) have on carbon dioxide content to be minimized. The actual solubilities and/or saturation pressures of the individual gases dissolved in the sample liquid may be ascertained and thus the content quantities of these gases also can be determined.

When the sample of liquid is expanded in the measuring chamber, a liquid phase and a gas phase form from the original single liquid phase in which all the gases are dissolved. Because of the very different solubilities of carbon dioxide, oxygen, and nitrogen in the sample liquid, the proportion of the partial pressures of the individual gases in the gas phase differs substantially from the proportion of the saturation pressures of the dissolved gases in the original (pre-expanded) sample liquid. The general principle is that the lower the solubility of a gas in a liquid, the more the partial pressure of the gas dissolved in the liquid will decrease as the volume is increased.

In order to determine the quantities of two or more gases dissolved in the sample liquid, two or more increase steps are implemented. After each of the volume increase steps, the equilibrium pressure then-established and the prevailing temperature are each measured. From the values ascertained are calculated the content quantities and, if desired, also the solubilities and/or saturation pressures of the individual gas components. As a result of a volume increase, on the basis of Henry's and Boyle's laws the following partial pressures occur in the gas phase:

$$p'=p/(1+k/(L*p_s))$$

p' is the partial pressure of a gas after the measuring chamber volume increase;
p is the original saturation pressure of the gas in the liquid;
k is the volume increase factor;
L is the solubility of the gas in the sample liquid; and
$p_s$ is standard pressure (1 bar).

Using the multiple-step volume expansion method described in Bloder et al. U.S. Pat. No. 6,874,351, the solubilities of carbon dioxide and/or other gases dissolved in the sample liquid also may be determined. This is particularly important when the content quantities of several gases dissolved in the sample liquid are to be determined and the solubilities of the individual dissolved gases to be determined in the actual liquid itself are not precisely known. This is often the case as the remainder of the composition of the sample liquid has a strong effect on the solubilities of the gases dissolved therein. For example, the solubilities of the aforementioned gases in an acidic beverage may be drastically different from those of the same gases in pure water.

If a gas dissolved in the sample liquid is present in a much greater quantity than all the other gases dissolved therein, and if the solubilities of the other gases are substantially lower and possibly even alike, these other gases may be treated as a single gas component. This is advantageous if, for example, as well as the carbon dioxide content of a sample, only the air content, for example, is to be determined or if only the effect of all the other dissolved gases on the ascertained carbon dioxide content is to be eliminated. In this case it is possible to use in the equation system for the "hypothetical" solubility of the "other" dissolved gases a weighted mean value of their actual solubilities.

If, for example, only the content and the solubility of $CO_2$ are sought, and oxygen and nitrogen are only dissolved to a minor degree, by means of two accordingly large volume increases, e.g., by 10% and by 20%, the effect of oxygen and nitrogen can be suppressed to the extent that it can be disregarded and no specific volume increase steps are necessary in order to take it into consideration. Because of the very low solubilities of oxygen and nitrogen, their partial pressures in the gas phase decrease markedly as a result of an increased volume increase and are no longer significant.

Because the solubility of gases in liquids is dependent to a considerable extent on temperature, apart from routine measurements with temperature conditions remaining virtually constant, it may be advisable to measure the temperature of the sample liquid and include it in the calculations. If the procedure involves only one measuring chamber in which the volume increase steps are performed one after the other, constancy of the measuring conditions is ensured in a simple manner.

Figure 2:
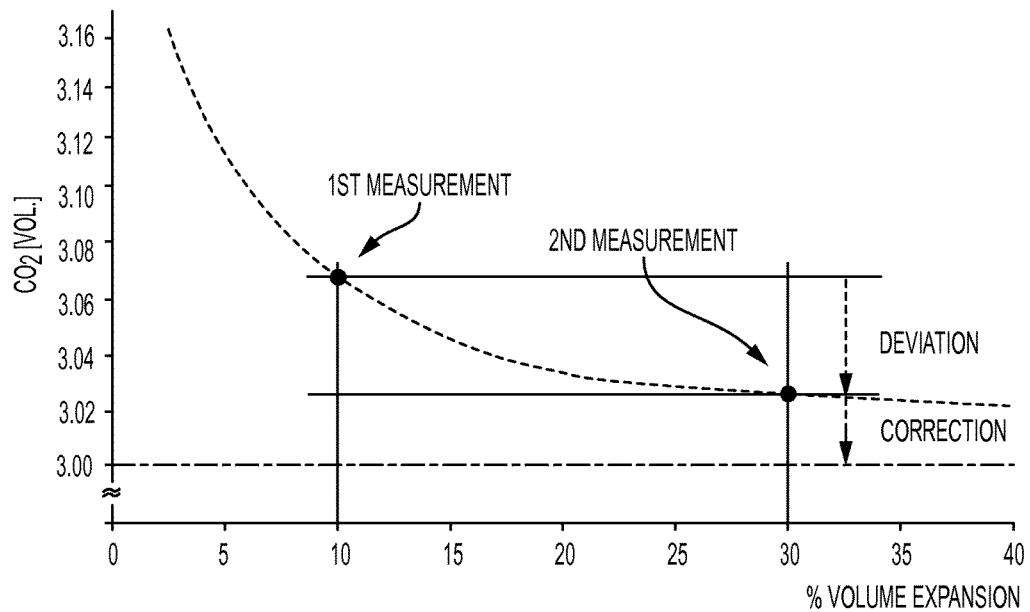
FIG. 2 is a graph illustrating a technique for compensating for dissolved gases such as oxygen and nitrogen during measurement of carbon dioxide levels.

FIG. 2 graphically illustrates the principle of multiple volume expansion for purposes of eliminating the influence of dissolved air and/or nitrogen on the measuring result. $CO_2$ content is measured at two different volume expansions of the measuring chamber, for example at 10% and 30%. If the two results are identical, it can be concluded that there is no dissolved air or nitrogen present, and therefore no correction is required. If dissolved air or nitrogen is present, the second result will be lower than the first. The difference between the two results then may be used to calculate a correction, thereby eliminating the influence of dissolved air or nitrogen on the measuring result.

In some examples, a piston-type injector may be used for increasing the volume of the measuring chamber. In other examples, a reproducibly deformable membrane, e.g., made of an elastomer or the like, may be used for expanding the volume of the measuring chamber. Yet other techniques also may be used for expanding the volume of the measuring chamber provided that that fluid-tightness is maintained during the volume expansion(s). In addition to making equilibrium pressure measurements as previously described, selective gas sensors also may be used to determine the content of individual gases dissolved in the liquid.

If desired, a power-regulated ultrasonic transducer may be used to promote cavitation effects while bringing about the desired establishment of the equilibrium pressure in the measuring chamber. The amount of ultrasonic energy used may be adapted to the particular liquid analyzed.

In use, the fluid-tight measuring chamber may be filled completely with the sample liquid and closed fluid-tight. One partial region of the boundary or wall of its interior space may be used for changing the volume of the interior space thereof. The position and/or the surface geometry of the partial region is varied, while fully retaining the fluid-tightness. When a membrane is used as the partial region, it initially may be positioned in a standard position and standard geometry. The membrane may be movable into, and/or deformable to, at least one defined location position and/or surface geometry, the effect of which is to produce an increase in the volume of the measuring chamber interior space corresponding in each case to an adjustable volume increase factor. If two or more gases dissolved in the liquid are to be selectively determined, a partial region of the interior space boundary or wall of the measuring chamber may be variable in its position and/or surface geometry such that it is movable into, and/or deformable to, at least two mutually differing defined location positions and/or surface geometries.

Another non-limiting example of a carbonation measurement device which employs pistons to create a volume expansion of the sample is described in Wieland et al. U.S. Pat. No. 4,726,769, the disclosure of which is hereby incorporated by reference in its entirety.

Figure 3:
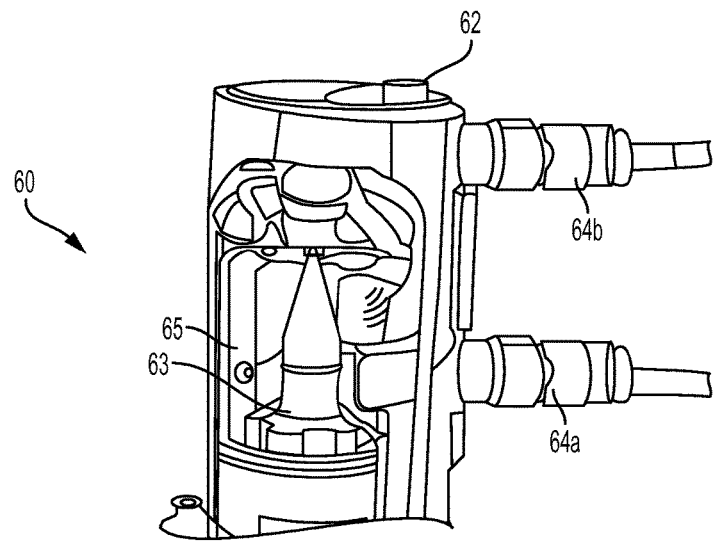
FIG. 3 is a schematic illustration of a measuring chamber that may be used in accordance with one embodiment of the invention.

FIG. 3 schematically illustrates a carbonation measurement device 60 having an inlet valve 64a for delivering a sample into a measuring chamber 65. The volume of the measuring chamber 65 may be expanded by actuation of a piston 63. A flow valve 62 allows for regulation of sample flow into the measuring chamber 65. After the measurements are completed, the sample is discharged from the measuring chamber 65 through an outlet valve 64b.

Figure 4:
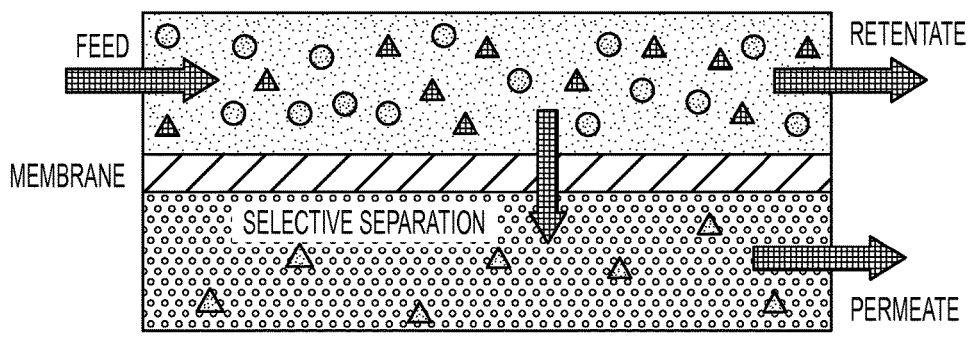
FIG. 4 schematically illustrates a selective membrane that may be used for measuring carbon dioxide levels in accordance with another embodiment of the invention.

A second type of measuring instrument that may be used involves a selective membrane, in particular one which is permeable to carbon dioxide but impermeable to other gases. After separating carbon dioxide from the remaining liquid and gaseous components in the sample, a suitable device may be used for determining the carbon dioxide level. For example, one type of device available from Hach Orbisphere employs thermal conductivity to measure the quantity of $CO_2$ that permeates through a selective membrane. The selective membrane acts as a filter to separate carbon dioxide from the sample and generate a $CO_2$-rich permeate, as shown schematically in FIG. 4. Two primary characteristics dictate membrane performance: permeability (the flux of a specific gas through the membrane) and selectivity (the membrane's preference to pass one gas species and not another). There are several possible mechanisms for membrane separation, including Knudson diffusion, molecular sieving, solution-diffusion separation, surface diffusion, and capillary condensation. Molecular sieving and solution diffusion are the main mechanisms for most gas separating membranes. Knudson separation is based on gas molecules passing through membrane pores small enough to prevent bulk diffusion. Separation is based on the difference in the mean path of the gas molecules due to collisions with the pore walls, which is related to the molecular weight. Specifically, the selectivity for any gas pair is determined by the inverse ratio of the square root of their molecular weight. For $CO_2/N_2$ separation, for example, Knudsen diffusion predicts a selectivity of less than unity.

Molecular sieving relies on size exclusion to separate gas mixtures. Pores within the membrane are of a controlled size relative to the kinetic (sieving) diameter of the gas molecule. This allows diffusion of smaller gases at a much faster rate than larger gas molecules. In this case, the $CO_2/N_2$, selectivity is greater than unity, as $CO_2$ has a smaller kinetic diameter than $N_2$. Surface diffusion is the migration of adsorbed gases along the pore walls of porous membranes. The rate of surface diffusion is determined by the level of interaction between the adsorbed gases and pore surface. Thus, molecules diffuse along the pore walls relative to the strength of this interaction, and separation is mainly achieved by the difference in the degree of this interaction for the individual gases. An extension of surface diffusion is when the vapor pressure becomes low, adsorbed gas can undergo partial condensation within the pores. This condensed component diffuses more rapidly through the pore than gases, causing separation of the condensable gas. This is known as capillary condensation.

Polymeric membranes are generally non-porous, and therefore gas permeation through them is characterized by the solution-diffusion mechanism. This is based on the solubility of specific gases within the membrane and their diffusion through the dense membrane matrix. Thus, separation is not just diffusion-dependent but also reliant on the physical-chemical interaction between the various gas species and the polymer, which determines the amount of gas that can accumulate in the membrane polymeric matrix.

A third type of measuring instrument that may be used involves passing a beam of infrared (IR) light through a liquid sample and measuring the angle of refraction to determine the carbonation level of the sample. The absorption of infrared radiation in a gas occurs at the atomic and molecular levels. In the case of $CO_2$, the polyatomic molecular structure determines the photon excitation modes and energy exchange rates, and hence, the wavelengths at which optical energy absorption occurs. Because this absorption effect occurs at the molecular level, the absorption of infrared radiation along a given transmission path depends on the number of molecules present. The amount of absorption at 4.26 micrometers is directly proportional to the molecular fraction of $CO_2$ present. Additionally, because pressure and temperature affect the density of the gas, the absorption is also dependent on the pressure and temperature at which the infrared absorption measurements are made.

This selective optical absorption phenomena has application as a method for determining the presence and amount of gaseous components dissolved in liquid. For example, a basic $CO_2$ sensing technique in common use employs an infrared radiation source (typically an incandescent lamp) and an infrared detector (typically a semiconductor photodiode) in a closed chamber in which gas samples are introduced for testing. A narrowband interference filter is used as the optical window of the photodiode detector to make it selective only to the 4.26 micrometer absorbing wavelength. For a given optical path length in the test chamber, the photodetector output can be calibrated using gas mixtures having a known $CO_2$ gas concentration to provide a useful instrument for sensing $CO_2$ dissolved in liquid samples. The basic sensitivity of this arrangement depends on the sharpness of the interference filter so as to minimize the amount of infrared radiation not related to $CO_2$ absorption reaching the detector, the optical path length containing the $CO_2$ molecules, the luminance stability of the infrared radiation source, and the stability of the detection response of the photodiode detector. Other factors that can affect the sensitivity and calibration accuracy of the method include possible turbulent flow in the gas sample passing through the test chamber, aging of the infrared radiation source and detector, and contamination accumulation on the source and detector optical windows.

Figure 5:
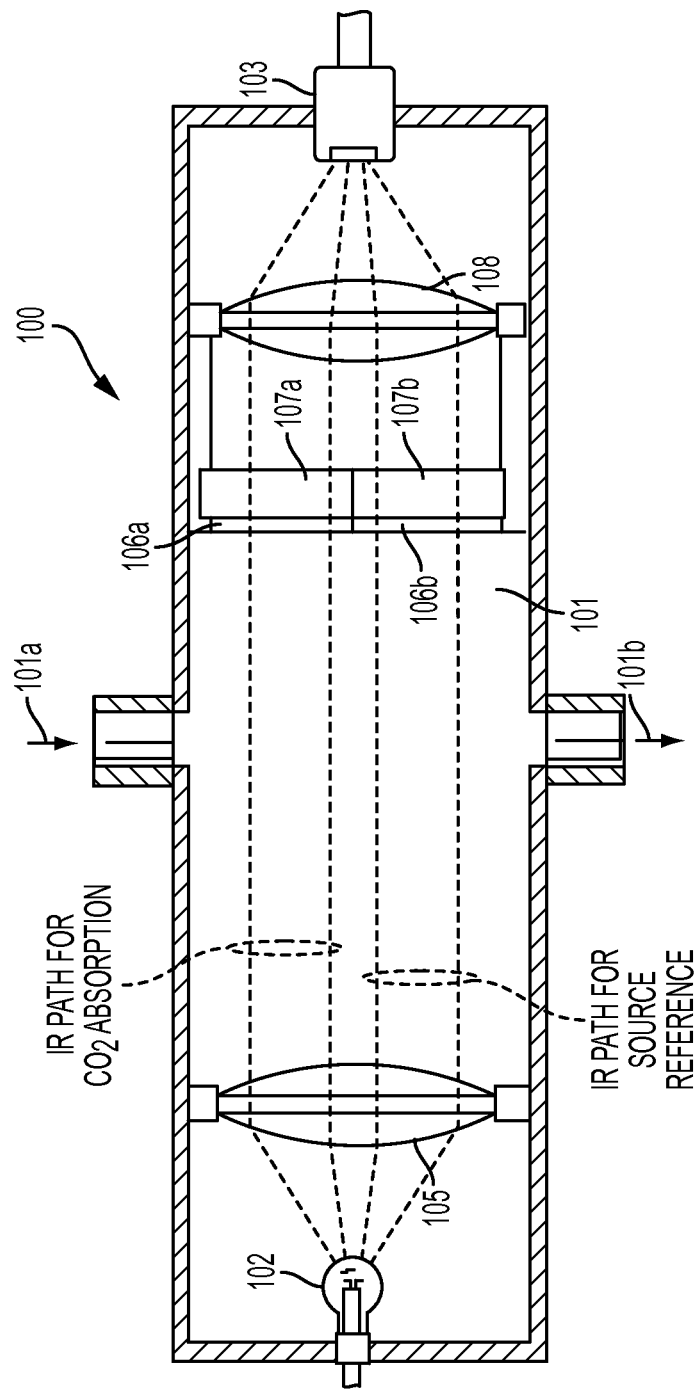
FIG. 5 schematically illustrates an infrared (IR) sensor that may be used for measuring carbon dioxide levels in accordance with yet another embodiment of the invention.

One example of an IR-based measuring instrument is shown schematically in FIG. 5. The compensated IR $CO_2$ sensor 100 has two optical paths but only a single IR radiation source 102 and a single IR radiation detector 103. A pair of fixed optical interference filters 106a and 106b in combination with an optical chopper 108 achieves separate and independent measurements at 4.26 micrometers (gas attenuating wavelength) and at 3.9 micrometers (reference wavelength). By normalizing the 4.26 micrometer absorption measurement with the 3.9 micrometer measurement, aging effects in the IR source 102 and in the detector 103, and to some extent, the effects of contamination of the optical windows, are compensated.

The sample may be introduced via an inlet 101 into chamber 101 and passed through outlet 101b post-measurement. The chamber 101 may be generally tubular in shape and have a circular cross sectional area. The interior elements, namely collimator lens 105, filters 106a and 106b, chopper 107, and focusing lens 108 can be made circular in shape to generally conform to the inner diameter of chamber 101. The collimator lens 105 collimates the infrared radiation from source 102. The focusing lens 108 focuses the radiation on detector 103. Lenses 105 and 108 are typically sapphire or germanium lenses.

Where chamber 101 is cylindrical, the filters 106a and 106b may each have a semicircular geometry. One filter filters a first half of the cross-section of the collimated radiation along the length of chamber 101 and the other filter filters the other half of the collimated radiation cross-section. One filter is selective to 3.9 micrometer wavelength and the other is selective to 4.26 micrometer wavelength. The effect of filters 106a and 106b is to split the radiation path in half, so that one half comprises 4.26 micrometer wavelength radiation and the other half comprises 3.9 micrometer wavelength radiation.

Choppers 107a and 107b chop the radiation passing through the filters 106a and 106b, respectively. The geometry of choppers 107a and 107b conforms to the geometry of filters 106a and 106b, such that each chopper has a semicircular geometry. Choppers 107a and 107b act as alternating shutters to block and pass the radiation transmitted through the filters 106a and 106b. They operate sequentially such that detector 103 sequentially and periodically receives a reference signal from filter 107a and a $CO_2$-attenuated signal from filter 107b (or vice versa).

Choppers 107a and 107b may be implemented with liquid crystal devices (LCDs), such as a two-section liquid crystal chopper. An LCD array may be used such that its top portion is used to chop the radiation from filter 106a and its bottom portion is used to chop the radiation from filter 106b. The two portions are thus independently operable.

Conventional electronic circuitry and processing devices (not shown) may be used to control choppers 107a and 107b and to normalize the 4.26 micrometer signal by the 3.9 micrometer signal. The attenuation of the signal through chopper 107b depends on the amount of $CO_2$ present in the optical path within chamber 101. Other details of the IR $CO_2$ sensor are disclosed in U.S. Pat. No. 6,969,857 to Owen, the disclosure of which is hereby incorporated by reference in its entirety.

Carbonation Measurement Vessel

A suitable carbonation vessel may be used to collect the open-container beverage and present it to the carbonation measuring instrument in an appropriate state for analysis. The carbonation vessel generally should be configured to preserve the state of the liquid with dissolved gases therein, and have a suitable closure (e.g., screw top or the like) to avoid gases from escaping from the sample and to avoid any ambient gases from becoming dissolved in the liquid sample.

Figure 6:
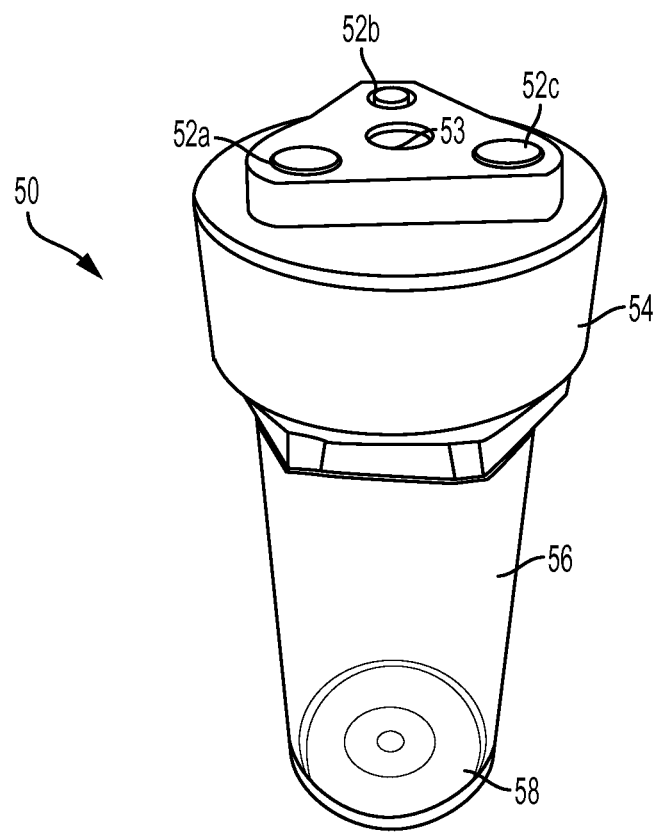
FIG. 6 is an isometric view of a carbonation measurement vessel that may be used in accordance with one embodiment of the invention.
Figure 7:
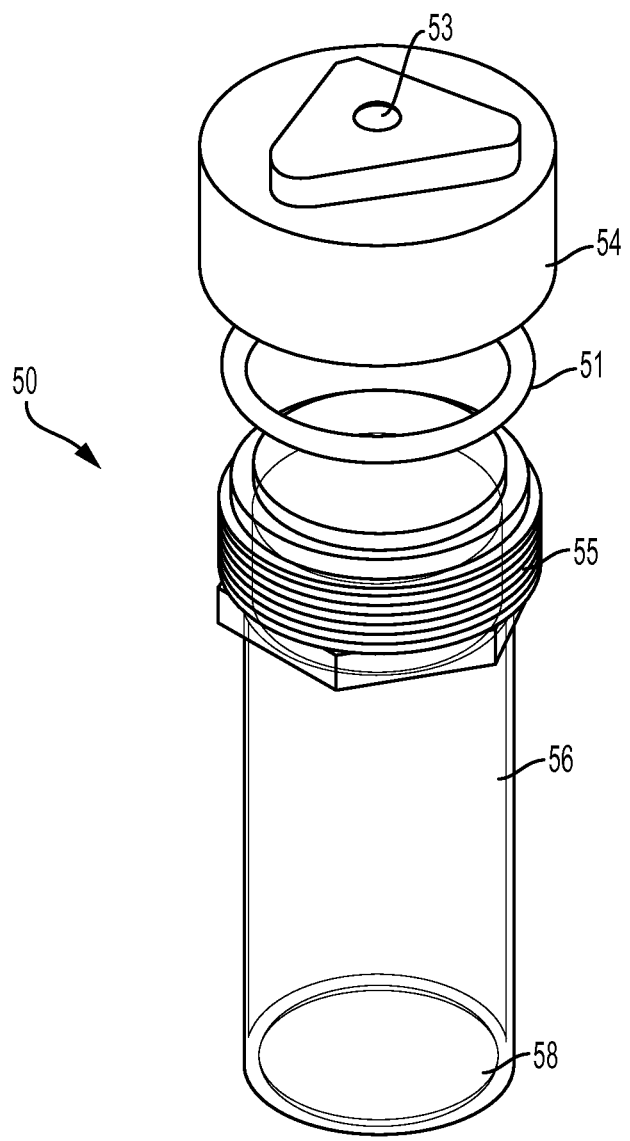
FIG. 7 is an isometric view of a carbonation measurement vessel with the threaded closure removed.

FIGS. 6 and 7 illustrate an example of a carbonation vessel 50 that may be used. The vessel 50 is a modified version of a carbonation vessel commercially available from TapRite (part nos. 2701-16A and 2701-15). The carbonation vessel 50 has a generally cylindrical container 56 for holding a volume of the beverage and a closure 54 which may be secured to form a fluid-tight enclosed volume. The vessel, as commercially available, has three apertures in the screw top 54 through which gauges (not shown) are received. In the modified version depicted in FIG. 6, the three apertures are sealed closed with covers 52a-52c. Another modification is that an aperture is formed in approximately the center of the closure 54 through which a valve 53 is placed. The valve 53 permits insertion of a probe (not illustrated) into the enclosed volume to extract a sample from the container 56, while otherwise maintaining fluid-tight conditions. As shown in FIG. 7, the closure 54 may be secured to the container body 56 by twisting over threads 55. A washer 51 may be provided to further promote a fluid-tight environment.

A further modification made relative to the commercially available vessel is that the shape of the bottom portion 58 of the vessel 50 may be modified so that the bottom portion 58 fits into the receptacle of a sample transfer device being used. For example, if a sample transfer device is configured to receive a standard sized 12 oz. can, the bottom portion 58 of the carbonation vessel 50 may have a shape corresponding to the bottom portion of a standard sized 12 oz. can so that the vessel 50 may be received into the receptacle of the sample transfer device.

While a threaded enclosure 54 is illustrated, any other suitable means may be used for securing the closure, such as a latch or other type of locking mechanism. Most often, a sample of the beverage is transferred from its existing container (or directly from a fountain dispensing device) into the vessel 50. However, if desired the beverage along with its existing container (e.g., a disposable cup with or without a lid) may be together placed into the vessel 50. In this situation, the probe would be inserted through the valve 53 and through the lid of the disposable cup (if present) into contact with the beverage.

Further, while the aperture for receiving the valve 53 is illustrated as being centered with respect to the upper surface of the enclosure 54, it should be recognized that various other configurations are possible, including positioning the aperture at a location of the enclosure 54 other than at the center of the upper surface. The aperture may be positioned at any location provided that it allows for appropriate transfer of the liquid sample.

A small bath container (not illustrated) holding an ice/water mixture, or other suitable type of heat exchanger, may be used to chill the carbonation vessel. Chilling the beverage sample may be advantageous to preserve as much dissolved $CO_2$ as possible in the sample volume.

Sample Transfer Device

One of the challenges presented when measuring carbonation levels, especially with respect to open-container beverages, is that sample transfer carries the risks of the loss of carbon dioxide and/or the dissolution of external gases into the liquid sample. To minimize these risks, it is advantageous to transfer samples using a filling system designed to prevent gas transfer to and from the liquid sample. Applying pressurized gas to the head space of the container, for example, reduces the risk of $CO_2$ loss from the sample. An example of a commercially available device that may be used is a Piercing and Filling Device (PFD), available from Anton Paar. The PFD has a probe (not illustrated) which is inserted through the valve 53 of the carbonation vessel. A sample of the beverage is transferred using a compressed inert gas, such that the amount of dissolved gas such as carbon dioxide and oxygen is not affected during the transfer.

EXAMPLE 1

The following example is provided for illustrative purposes and should not be regarded as limiting the scope of the present invention. With reference to the flow diagram shown in FIG. 1, this example illustrates a method of measuring carbonation levels in opened soft drink cans using the previously described Anton Paar CarboQC instrument equipped with a Piercing and Filling Device (PFD).

Initially, the sample flow should be checked. With reference to FIG. 3, the flow through the measuring chamber 65 should be such that approximately 150 mL of sample are consumed when the filling time is set to approximately 30 seconds. The flowrate may be adjusted by turning the flow valve 62 clockwise for decreased and counterclockwise for increased sample flow. Considerably lower or higher flow rates may cause erroneous measurements due to sample carry-over or gas bubbles in the measuring chamber 65. Flowrate should be adjusted, as needed, prior to starting of testing but does not need to be checked prior to every operation. The minimum flush volume should be at least 150 mL, 100 mL for identical samples. The minimum flush time should be no shorter than 20 seconds or longer than 35 seconds.

A beaker or graduated cylinder may be used to check the flowrate as follows. Insert the T-hose connector of the sample outlet hose 64*b* into a beaker which has been filled with at least 150 mL of DI water. Select the menu "instrument>rinse" and set the rinsing time to 30 seconds. Position the flow valve 62 at about 10% flow, i.e., close to the minimum flow position. Carry out a measurement as described below. Check the volume of liquid consumed (it should be 150 mL). If the volume is not in the required range, slightly open or close the flow valve 62 or adjust rinse time and repeat these steps until the volume is within the required range.

A marked bottle may be used to check the flowrate as follows. Make volume markings "0" and "150 mL" on a transparent 0.5 L (16 oz.) or similar size PET bottle. Use water and a graduated cylinder or a balance to correctly place these markings on the bottle. Fill the bottle up to the "0" mark with deionized water and close it. Insert the bottle into the PFD. Select the menu "instrument>rinse" and set the rinsing time to 30 seconds. Position the flow valve 62 at about 10% flow, i.e., close to the minimum flow position. Carry out a measurement as described below. Check the volume of liquid consumed (it should be 150 mL). If the volume is not in the required range, slightly open or close the flow valve 62 or adjust rinse time and repeat these steps until the volume is within the required range.

Weighing may be used to check the flowrate as follows. Weigh a full beverage bottle or can and make a note of the weight. Insert the package into the PFD. Select the menu "instrument>rinse" and set the rinsing time to 30 seconds. Position the flow valve 62 at about 10% flow, i.e., close to the minimum flow position. Carry out a measurement as described below. Remove the package from the PFD and weigh it again. The weight should have decreased by 150 g.

Measurement Procedure

When collecting the carbonation sample from the system into the carbonation vessel, it should be recognized that the transfer process may impact the carbonation reading. The method for collecting the sample from the system should be standardized for that system to ensure consistent readings. It is desirable to fill sample to the top of the container. After the sample is collected into the carbonation vessel, handle the carbonation vessel very gently when moving to the PFD to reduce any impact on carbonation.

Begin by preparing a small ice/water bath. Place the bottom of the carbonation vessel into the ice/water bath for at least 10 minutes.

Move the sample tube of the PFD to the highest position. Push the safety shield upwards completely. Remove the PET bottle adapter. Adjust the position of the piercing head, if necessary. Retrieve the bottom of the carbonation vessel from the ice bath. Shake the remaining water off the bottom of the carbonation vessel. Acquire a carbonation sample from the system that is being measured. Place the bottom of carbonation vessel on a level surface and screw on the cap tightly. Insert the carbonation vessel into the PFD (the bottom should fit snugly in the cut-out). Push the safety shield down until the safety pin engages. Hold the safety shield down and pull the activating lever. Lower the sample tube of the PFD into the carbonation vessel until it is approximate ¼" from bottom of the carbonation vessel (avoid touching the bottom) and then fasten the sample tube.

Next, select the appropriate method on the carbonation measuring instrument for the sample being tested (e.g., sugar soft drink, diet soft drink, etc.). The different methods account for the different solubility of carbon dioxide in different beverages. Custom methods may be created to account for the distribution of carbon dioxide between headspace gas and the liquid present in bottles or cans.

Press <Start> to begin the measurement. The measuring chamber is first rinsed and filled with 150 mL of the new sample. Visually inspect the measuring chamber to ensure a bubble-free sample flow. If the bubbles do not disappear after approximately 15 seconds, the filter may require cleaning. Check the pressure of the compressed gas supply. It should be 6±0.5 bar relative (87±7 psi).

Once the rinsing is finished, the analysis will begin. The piston will move down to a first halt and then to a second halt with the stirrer in continuous operation. If the sample has a high content of particles (e.g., pulp), the sieve of the filter tends to clog. This may tend to lower the pressure in the measuring chamber. Check the pressure during sample filling. When using a PFD, the pressure should not go below 5 bar (70 psia). If the sieve is completely clogged, bubbles and foam form in the hose between filter and measuring chamber and in the measuring chamber itself.

Wait approximately 90 seconds for the measurement result. The measurement result will be displayed, stored in the memory and, if desired, printed out. The piston will then move up, but the measuring chamber will remain closed.

At the PFD, move the sample tube up to the highest position and fasten it. Push the activating lever to de-energize the system. Move the safety shield up to the highest position and remove the carbonation vessel. Optionally, check with a balance whether the correct amount of sample was taken from the bottle or can.

If no further measurements are to be performed, clean the system. If the instrument is not in use for more than 30 minutes after the last sample measurement, rinse the instrument with deionized water. Regular zero point checks with deionized water help ensure proper functionality of the instrument. A zero point check carried out with deionized water should be 0±0.02 vol (0±0.03 g/L). If the zero point check and adjustment are carried out with water that contains $CO_2$, the consequence will be an unjustified offset.

Only transfer equilibrated samples should be transferred to the measuring chamber. If samples are not equilibrated (shaken) prior to analysis, the consequence might be erroneous results or poor repeatability.

The filling pressure displayed on the CarboQC display should be 5.5 to 6 bar relative (79 psi to 87 psi) and the measuring chamber should be filled without bubbles. Too low sample pressures during sample filling may cause bubbles in the sample chamber. As a consequence, the starting volume will include gas bubbles thus yielding incorrect results.

Table 1 below presents single- and multi-laboratory validation data based on canned Pepsi® brand soft drink. For multi-lab with cans, with average gas volume of 3.6 and 2% RSD of 1% (measured via standard CarboQC procedure, TM200.082), one should expect carbonations measured via this procedure (AMS-001) to have average gas volume of 3.4 with 2% RSD of 2.71%, provided the cans are refrigerated. Single lab results are similar: average gas volume of 3.62 with 2% RSD of 0.17% via TM200.082 and 3.43 with 2% RSD of 2.26% via AMS-001.

Table 2 below presents data for Mountain Dew® brand soft drink. The multi-lab results suggest a minimum difference between the two methods. For TM200.082, the average gas volume was 2.41 with 2% RSD of 1.68%, while for AMS-001 the average was 2.35 with 2% RSD of 1.69%.

TABLE 1

| Pepsi® | | | | |
|---|---|---|---|---|
| | Multi Lab | | Single Lab | |
| | TM200.082 | AMS-001 | TM200.082 | AMS-001 |
| Average | 3.60 | 3.40 | 3.62 | 3.43 |
| Pooled Standard Deviation | 0.0179 | 0.0460 | 0.0194 | 0.0387 |
| 2% RSD | 1.00% | 2.71% | 1.07% | 2.26% |

TABLE 2

| Mountain Dew® | | |
|---|---|---|
| | Multi Lab | |
| | TM200.082 | AMS-001 |
| Average | 2.41 | 2.35 |
| Pooled Standard Deviation | 0.0202 | 0.0199 |
| 2% RSD | 1.68% | 1.69% |

The foregoing description should be considered illustrative rather than limiting. It should be recognized that various modifications can be made without departing from the spirit or scope of the invention as described and claimed herein.

What is claimed:

1. A method of measuring carbon dioxide volume levels in an open-container beverage, the method comprising:
   providing an open-container beverage in an open container;
   transferring a quantity of the beverage from the open container to a vessel different from the open container to at least partially fill the vessel;
   securing a closure onto the vessel to form an enclosed volume containing the quantity of the beverage;
   inserting a probe through the closure to contact the beverage;
   transferring a sample of the beverage from the vessel to a carbon dioxide measurement instrument; and
   quantitatively determining the carbon dioxide volume level of the sample.

2. The method of claim 1, further comprising a step of reducing the temperature of the beverage contained in the vessel.

3. The method of claim 2, wherein the temperature of the beverage is reduced by placing the vessel in an ice bath.

4. The method of claim 1, wherein the carbon dioxide level of the sample is determined by the steps of:
   placing the sample in an expandable measurement chamber;
   expanding a volume of the measurement chamber; and
   measuring an equilibrium pressure of the expanded volume.

5. The method of claim 4, wherein the volume of the measurement chamber is expanded by displacing a piston-type injector fitted fluid-tight to the measurement chamber.

6. The method of claim 4, wherein the volume of the measurement chamber is expanded by displacing a flexible membrane.

7. The method of claim 6, wherein the membrane is constructed from an elastomer.

8. The method of claim 4, further comprising the steps of:
   expanding the volume of the measurement chamber to a second expanded volume; and
   measuring an equilibrium pressure in the second expanded volume.

9. The method of claim 4, further comprising a step of applying ultrasonic energy to the measurement chamber.

10. The method of claim 1, further comprising a step of applying pressurized gas to the head space of the vessel.

11. The method of claim 1, wherein the carbon dioxide level of the sample is determined by the steps of:
    contacting the sample with a $CO_2$-selective membrane; and
    measuring the amount of permeate passing through the membrane.

12. The method of claim 1, wherein the carbon dioxide level of the sample is determined by the steps of:
    passing infrared radiation through the sample; and
    measuring the angle of refraction to determine the carbon dioxide level.

13. The method of claim 1, wherein the beverage is a carbonated soft drink.

14. The method of claim 1, wherein the beverage is carbonated water.

15. The method of claim 1, wherein the beverage is provided in an opened can.

16. The method of claim 1, wherein the beverage is provided in an opened bottle.

17. The method of claim 1, wherein the beverage is dispensed from a fountain dispensing device.

18. The method of claim 17, wherein the beverage is provided in a disposable cup, and the disposable cup together with the beverage are placed into the vessel.

* * * * *